US012609204B2

(12) United States Patent
Ma et al.

(10) Patent No.: US 12,609,204 B2
(45) Date of Patent: Apr. 21, 2026

(54) SYSTEMS AND METHODS FOR USING MACHINE LEARNING ALGORITHMS TO IDENTIFY CARE GAPS

(71) Applicant: Aetna Inc., Hartford, CT (US)

(72) Inventors: Yechi Ma, Hartford, CT (US); Wesley Huang, Hartford, CT (US); Abdulkadir Hallac, Hartford, CT (US)

(73) Assignee: Aetna Inc., Hartford, CT (US)

( * ) Notice: Subject to any disclaimer, the term of this patent is extended or adjusted under 35 U.S.C. 154(b) by 649 days.

(21) Appl. No.: 17/992,755

(22) Filed: Nov. 22, 2022

(65) Prior Publication Data

US 2024/0170154 A1     May 23, 2024

(51) Int. Cl.
*G16H 50/30*       (2018.01)
*G16H 10/60*       (2018.01)
*G16H 20/00*       (2018.01)

(52) U.S. Cl.
CPC ............. *G16H 50/30* (2018.01); *G16H 10/60* (2018.01); *G16H 20/00* (2018.01)

(58) Field of Classification Search
None
See application file for complete search history.

(56) References Cited

U.S. PATENT DOCUMENTS

| | | | |
|---|---|---|---|
| 6,802,810 B2 | 10/2004 | Ciarniello et al. | |
| 7,828,205 B2 | 11/2010 | Cronin et al. | |
| 10,628,047 B2 | 4/2020 | Mooney et al. | |
| 11,373,248 B1 * | 6/2022 | Criswell | ................ G06Q 40/08 |
| 11,631,484 B1 * | 4/2023 | Hanina | .................. G16H 80/00 |
| | | | 706/11 |
| 2008/0287746 A1 | 11/2008 | Reisman | |
| 2009/0216558 A1 | 8/2009 | Reisman et al. | |
| 2009/0228304 A1 | 9/2009 | Ciarniello et al. | |
| 2013/0179178 A1 | 7/2013 | Vemireddy et al. | |
| 2017/0109479 A1 | 4/2017 | Vemireddy et al. | |
| 2023/0087969 A1 * | 3/2023 | Fornwalt | ................ G16H 10/20 |
| | | | 705/2 |
| 2024/0143591 A1 * | 5/2024 | Diaz-Castillo | .... G06F 16/24547 |

OTHER PUBLICATIONS

Meredith O'Connor et al., Better together: Advancing life course research through multi-cohort analytic approaches, Advances in Life Course Research, vol. 53, Sep. 2022, 100499, https://doi.org/10.1016/j.alcr.2022.100499. (Year: 2022).*

* cited by examiner

*Primary Examiner* — Devin C Hein
(74) *Attorney, Agent, or Firm* — Leydig, Voit & Mayer, Ltd.

(57) ABSTRACT

In some instances, a method is provided. The method comprises obtaining one or more care gap machine learning-artificial intelligence (ML-AI) models; obtaining individual information of an individual, wherein the individual information indicates one or more medical conditions of the individual and personal information of the individual; determining care gap information of the individual based on using the one or more care gap ML-AI models and the individual information, wherein the care gap information indicates one or more predictions for expectancy of a care gap of the individual, and wherein the care gap is associated with a gap in time that the individual has a lapse in receiving medical care for the one or more medical conditions; and performing one or more care gap interventions based on the care gap information.

20 Claims, 6 Drawing Sheets

100

202

Bus

Processor     ⌇ 204

ROM          ⌇ 206

RAM          ⌇ 208

Storage      ⌇ 210

Network
Interface    ⌇ 212

200

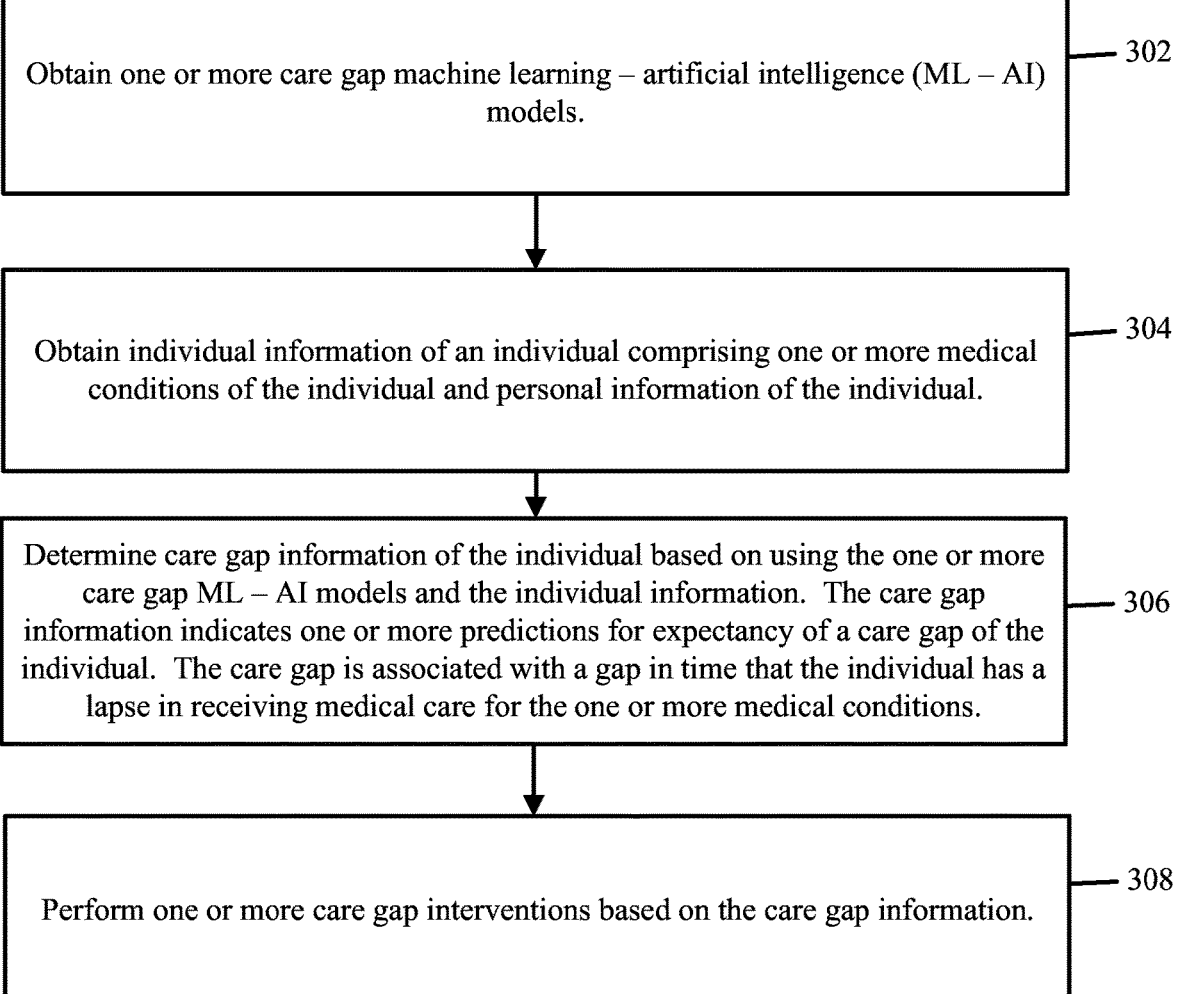

Obtain one or more care gap machine learning – artificial intelligence (ML – AI) models. ⎯ 302

Obtain individual information of an individual comprising one or more medical conditions of the individual and personal information of the individual. ⎯ 304

Determine care gap information of the individual based on using the one or more care gap ML – AI models and the individual information. The care gap information indicates one or more predictions for expectancy of a care gap of the individual. The care gap is associated with a gap in time that the individual has a lapse in receiving medical care for the one or more medical conditions. ⎯ 306

Perform one or more care gap interventions based on the care gap information. ⎯ 308

Expectancy of Care Gap

|          | 1.0   | 2.0   | 3.0   | 4.0   | 5.0   | 6.0   | 7.0   | 8.0   | 9.0   | 10.0  | 11.0  | 12.0  |
|----------|-------|-------|-------|-------|-------|-------|-------|-------|-------|-------|-------|-------|
| Member A | 13.9% | 26.0% | 38.6% | 49.4% | 56.5% | 65.7% | 70.4% | 74.3% | 77.3% | 80.3% | 82.1% | 84.1% |
| Member B | 17.5% | 32.1% | 46.6% | 58.4% | 65.8% | 74.8% | 79.1% | 82.6% | 85.2% | 87.6% | 89.1% | 90.7% |
| Member C | 13.0% | 24.5% | 36.5% | 47.0% | 54.0% | 63.1% | 67.8% | 71.9% | 75.0% | 78.0% | 79.9% | 82.1% |
| Member D | 16.8% | 31.0% | 45.2% | 56.8% | 64.2% | 73.3% | 77.7% | 81.3% | 84.0% | 86.5% | 88.1% | 89.7% |
| Member E | 15.2% | 28.4% | 41.7% | 53.0% | 60.2% | 69.4% | 74.0% | 77.8% | 80.7% | 83.4% | 85.2% | 87.0% |

SYSTEMS AND METHODS FOR USING MACHINE LEARNING ALGORITHMS TO IDENTIFY CARE GAPS

BACKGROUND

In some instances, an individual (e.g., a member or a patient) may experience a gap in care for a particular medical condition. For instance, the individual may suffer from a chronic medical condition such as diabetes or atherosclerotic cardiovascular disease. To monitor their medical condition (e.g., a chronic medical condition), the individual may visit their medical provider at set time intervals (e.g., every few months). Unfortunately, due to certain situations, the individual may miss one of these medical provider visits and a care gap may form. The care gap may indicate a scenario when the individual experiences a literal time gap in the care for a given medical condition. The longer the care gap, the more likely this individual is at risk for exacerbation of their illness and worsening health. As such, being able to predict when an individual is expected to "close" or "open" a care gap for a given medical condition and taking preventive actions against it can significantly mitigate or even prevent exacerbation of their illness and worsening health. Accordingly, there remains a technical need to determine, identify, or predict care gaps for individuals such that preemptive action (e.g., a medical treatment including a visit to a medical provider) can be taken.

SUMMARY

In some examples, the present application is capable of performing care management for individuals by being able to accurately predict in the future when a given individual will close or open a care gap for a given medical condition (e.g., a chronic condition). The present application may use one or more machine learning and/or artificial intelligence (ML-AI) algorithms or models (e.g., a survival analysis ML-AI model). For instance, the survival analysis ML-AI model may provide a model output indicating a gap closure or gap opening probability within a time span. Using the model output, the present application may be able to more effectively and efficiently target high risk individuals in care management initiatives.

For instance, the present application may train one or more care gap ML-AI models based on data from a plurality of data sources. Each care gap ML-AI model may be associated with one or more medical conditions (e.g., a particular medical condition). Based on inputting an individual's information (e.g., individual information of an individual) into the trained care gap ML-AI model, the care gap ML-AI model may provide model outputs (e.g., care gap information) indicating care gap predictions for the individual. For instance, the care gap prediction may include one or more probabilities indicating the likelihood that an individual may open or close their care gap within a certain time span. For instance, the care gap prediction may include twelve probabilities indicating the likelihood that the individual will open or close their care gap within the next year (e.g., one probability per month). Afterwards, care gap interventions may be performed based on the probabilities from the care gap ML-AI model. For instance, the care gap interventions may indicate for a telephone call (e.g., automated telephone call or a person calling the individual), text, email, or other message to be placed or sent to the individual after a certain amount of time has elapsed and the care gap is still not closed. This and other aspects will be described in further detail below.

In one aspect, a method is provided. The method comprises: obtaining, by a computing platform, one or more care gap machine learning-artificial intelligence (ML-AI) models; obtaining, by the computing platform, individual information of an individual, wherein the individual information indicates one or more medical conditions of the individual and personal information of the individual; determining, by the computing system, care gap information of the individual based on using the one or more care gap ML-AI models and the individual information, wherein the care gap information indicates one or more predictions for expectancy of a care gap of the individual, and wherein the care gap is associated with a gap in time that the individual has a lapse in receiving medical care for the one or more medical conditions; and performing, by the computing system, one or more care gap interventions based on the care gap information.

Examples may include one of the following features, or any combination thereof. For instance, in some examples, obtaining the one or more care gap ML-AI models comprises obtaining a plurality of care gap ML-AI models, wherein each of the plurality of care gap ML-AI models is associated with a particular medical condition, and wherein determining the care gap information of the individual comprises: selecting a care gap ML-AI model, from the plurality of care gap ML-AI models, based on comparing the one or more medical conditions of the individual and the particular medical condition associated with each of the plurality of care gap ML-AI models; and using the selected care gap ML-AI model and the individual information to determine the care gap information of the individual.

In some instances, obtaining the one or more care gap ML-AI models comprises obtaining a plurality of closed care gap ML-AI models, wherein each of the plurality of closed care gap ML-AI models is associated with a care gap cohort associated with a care gap time period, and wherein determining the care gap information of the individual comprises: selecting a closed care gap ML-AI model, from the plurality of closed care gap ML-AI models, based on comparing the gap in time that the individual has a lapse in receiving the medical care for the one or more medical conditions with the care gap cohort associated with each of the plurality of closed care gap ML-AI models; and using the selected closed care gap ML-AI model and the individual information to determine the care gap information of the individual.

In some variations, selecting the closed care gap ML-AI model, from the plurality of closed care gap ML-AI models, is further based on the one or more medical conditions of the individual.

In some examples, the individual information of the individual indicates a business segment associated with the individual, and selecting the closed care gap ML-AI model, from the plurality of care gap ML-AI models, is further based on the business segment associated with the individual.

In some instances, obtaining individual information of the individual comprises: receiving the individual information of the individual from an external source, wherein the personal information of the individual comprises financial information associated with the individual and prescription information of the individual.

In some variations, the one or more care gap ML-AI models comprises a closed care gap ML-AI model, and performing the one or more care gap interventions based on the care gap information comprises: displaying a plurality of probabilities indicating a likelihood of the individual closing the care gap within a time span.

In some examples, the one or more care gap ML-AI models comprises an open care gap ML-AI model, and performing the one or more care gap interventions based on the care gap information comprises: displaying a plurality of probabilities indicating a likelihood of the individual opening the care gap within a time span.

In some instances, the method further comprises: obtaining population information for a plurality of individuals associated with an enterprise organization; and training, using the population information, a plurality of care gap ML-AI models, wherein each of the plurality of ML-AI models is associated with a particular medical condition and a care gap cohort indicating a time period, wherein determining the care gap information of the individual comprises: selecting the one or more care gap ML-AI models from the plurality of care gap ML-AI models.

In some variations, the method further comprises: based on a triggering event, re-training the plurality of care gap ML-AI models using new population information.

In some examples, training the plurality of care gap ML-AI models comprises: modifying the population information to generate modified population information; and training the plurality of care gap ML-AI models using the modified population information.

In some instances, modifying the population information comprises: filtering the population information based on a plurality of medical conditions and a plurality of care gap cohorts to generate the modified population information.

In some variations, modifying the population information comprises: performing data manipulation to generate the modified population information, wherein the data manipulation comprises removal of nulls, feature filtration, or outlier removal.

In some examples, the one or more care gap ML-AI models comprises a survival analysis ML-AI model.

In some instances, obtaining the one or more care gap ML-AI models comprises obtaining a plurality of open care gap ML-AI models, wherein each of the plurality of open care gap ML-AI models is associated with a care gap cohort indicating a time period with a closed care gap, and wherein determining the care gap information of the individual comprises: selecting an open care gap ML-AI model, from the plurality of open care gap ML-AI models, based on comparing a length in time that the individual has accumulated the closed care gap with the care gap cohort associated with each of the plurality of open care gap ML-AI models; and using the selected open care gap ML-AI model and the individual information to determine the care gap information of the individual.

In another aspect, a computing platform comprising one or more processors and non-transitory computer-readable medium having processor-executable instructions stored thereon is provided. The processor-executable instructions, when executed by the one or more processors, facilitate: obtaining one or more care gap machine learning-artificial intelligence (ML-AI) models; obtaining individual information of an individual, wherein the individual information indicates one or more medical conditions of the individual and personal information of the individual; determining care gap information of the individual based on using the one or more care gap ML-AI models and the individual information, wherein the care gap information indicates one or more predictions for expectancy of a care gap of the individual, and wherein the care gap is associated with a gap in time that the individual has a lapse in receiving medical care for the one or more medical conditions; and performing one or more care gap interventions based on the care gap information.

Examples may include one of the following features, or any combination thereof. For instance, in some examples, obtaining the one or more care gap ML-AI models comprises obtaining a plurality of care gap ML-AI models, wherein each of the plurality of care gap ML-AI models is associated with a particular medical condition, and wherein determining the care gap information of the individual comprises: selecting a care gap ML-AI model, from the plurality of care gap ML-AI models, based on comparing the one or more medical conditions of the individual and the particular medical condition associated with each of the plurality of care gap ML-AI models; and using the selected care gap ML-AI model and the individual information to determine the care gap information of the individual.

In some instances, obtaining the one or more care gap ML-AI models comprises obtaining a plurality of closed care gap ML-AI models, wherein each of the plurality of closed care gap ML-AI models is associated with a care gap cohort associated with a care gap time period, and determining the care gap information of the individual comprises: selecting a closed care gap ML-AI model, from the plurality of closed care gap ML-AI models, based on comparing the gap in time that the individual has a lapse in receiving the medical care for the one or more medical conditions with the care gap cohort associated with each of the plurality of closed care gap ML-AI models; and using the selected closed care gap ML-AI model and the individual information to determine the care gap information of the individual.

In some variations, obtaining the one or more care gap ML-AI models comprises obtaining a plurality of open care gap ML-AI models, wherein each of the plurality of open care gap ML-AI models is associated with a care gap cohort indicating a time period with a closed care gap, and determining the care gap information of the individual comprises: selecting an open care gap ML-AI model, from the plurality of open care gap ML-AI models, based on comparing a length in time that the individual has accumulated the closed care gap with the care gap cohort associated with each of the plurality of open care gap ML-AI models; and using the selected open care gap ML-AI model and the individual information to determine the care gap information of the individual.

In yet another aspect, a non-transitory computer-readable medium having processor-executable instructions stored thereon is provided. The processor-executable instructions, when executed, facilitate: obtaining one or more care gap machine learning-artificial intelligence (ML-AI) models; obtaining individual information of an individual, wherein the individual information indicates one or more medical conditions of the individual and personal information of the individual; determining care gap information of the individual based on using the one or more care gap ML-AI models and the individual information, wherein the care gap information indicates one or more predictions for expectancy of a care gap of the individual, and wherein the care gap is associated with a gap in time that the individual has a lapse in receiving medical care for the one or more medical conditions; and performing one or more care gap interventions based on the care gap information.

5

All examples and features mentioned above may be combined in any technically possible way.

BRIEF DESCRIPTION OF THE DRAWINGS

The subject technology will be described in even greater detail below based on the exemplary figures, but is not limited to the examples. All features described and/or illustrated herein can be used alone or combined in different combinations. The features and advantages of various examples will become apparent by reading the following detailed description with reference to the attached drawings which illustrate the following:

FIG. 3 is an exemplary process for using the care gap ML-AI model to identify care gaps in accordance with one or more examples of the present application.

FIG. 5 shows exemplary care gap information based on using the care gap ML-AI model in accordance with one or more examples of the present application.

DETAILED DESCRIPTION

Examples of the presented application will now be described more fully hereinafter with reference to the accompanying FIGS., in which some, but not all, examples of the application are shown. Indeed, the application may be exemplified in different forms and should not be construed as limited to the examples set forth herein; rather, these examples are provided so that the application will satisfy applicable legal requirements. Where possible, any terms expressed in the singular form herein are meant to also include the plural form and vice versa, unless explicitly stated otherwise. Also, as used herein, the term "a" and/or "an" shall mean "one or more" even though the phrase "one or more" is also used herein. Furthermore, when it is said herein that something is "based on" something else, it may be based on one or more other things as well. In other words, unless expressly indicated otherwise, as used herein "based on" means "based at least in part on" or "based at least partially on".

Figure 1:
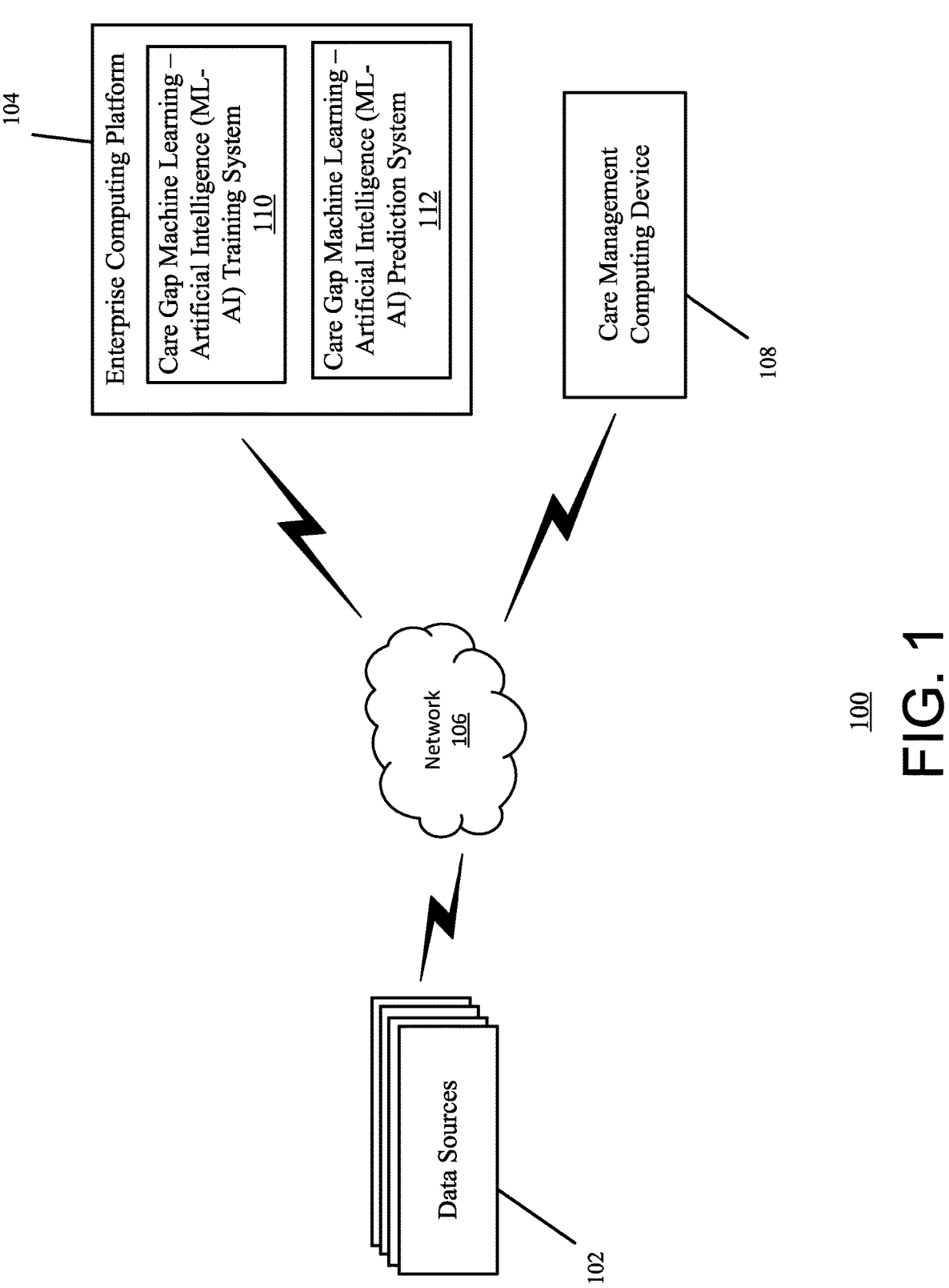
FIG. 1 is a simplified block diagram depicting an exemplary computing environment in accordance with one or more examples of the present application.

Systems, methods, and computer program products are herein disclosed that use one or more ML-AI models to identify care gaps. FIG. 1 is a simplified block diagram depicting an exemplary environment in accordance with an example of the present application. The environment 100 includes a plurality of data sources 102, an enterprise computing platform 104, and a care management computing device 108. The enterprise computing platform 104 includes a care gap machine learning-artificial intelligence (ML-AI) training system 110 and a care gap ML-AI prediction system 112. Although the entities within environment 100 may be described below and/or depicted in the FIGS. as being singular entities, it will be appreciated that the entities and functionalities discussed herein may be implemented by and/or include one or more entities. For instance, the training system 110 and the prediction system 112 may be separate computing entities located in separate geographic locations that use the network 106 to communicate between each other, as well as other devices or entities within environment 100. Additionally, and/or alternatively, a singular system (e.g., a singular computing system or device) may be configured to perform the functionalities of both the training system 110 and the prediction system 112.

The entities within the environment 100 such as data sources 102, the enterprise computing platform 104, and the care management computing device 108 may be in communication with other systems or facilities within the environment 100 via the network 106. The network 106 may be a global area network (GAN) such as the Internet, a wide area network (WAN), a local area network (LAN), or any other type of network or combination of networks. The network 106 may provide a wireline, wireless, or a combination of wireline and wireless communication between the entities within the environment 100. In some instances, the training system 110 and the prediction system 112 may use the network 106 to communicate with each other and other entities within environment 100. In other instances, the training system 110 and the prediction system 112 may communicate with each other and/or other entities within environment 100 (e.g., the enterprise computing platform 104) without using the network 106 (e.g., via communication protocols such as WI-FI or BLUETOOTH).

Each of the data sources 102 is and/or includes one or more computing devices, platforms, and/or systems that are configured to provide information (e.g., data files or other types of information) to the enterprise computing platform 104. For example, the data sources 102 are and/or include one or more computing devices, computing platforms, systems, servers, desktops, laptops, tablets, mobile devices (e.g., smartphone device, or other mobile device), or any other type of computing device that generally comprises one or more communication components, one or more processing components, and one or more memory components.

The data sources 102 are capable of performing tasks, functions, and/or other actions associated with an enterprise organization. The data sources 102 may receive, generate, and/or otherwise obtain information associated with a plurality of individuals (e.g., members). Furthermore, the data sources 102 may store the information associated with the individuals. For instance, the data sources 102 may be and/or include an enterprise data warehouse (EDW), a production warehouse (PROD), a clinical stratification and identification warehouse (CSID), an Active Health Management warehouse (AHM), an external data warehouse, and/or one or more computing platforms (e.g., cloud computing platforms). The EDW may be a data warehouse that stores data for a plurality of individuals (e.g., members associated with the enterprise organization). For instance, the EDW may store identifiers for the members/individuals, control features, and/or member demographics (e.g., age, gender, and so on). The PROD may store risk scores for the plurality of individuals (e.g., risk scores associated with commercial members and/or Medicare members). The AHM may store historical care gap information, records, procedures as well as other important information associated with the individuals (e.g., care gap market, procedure records, lab records, prescription records for the individuals). The CSID may store health management information for the members/individuals such as member care gap status, gap information (e.g., identifier, title, description for the members), effective date for membership, and/or other information. The external data warehouse may store social determinant of health (SDOH) information for the individuals/members. The data sources 102 listed above are merely exemplary and the data sources 102 may include additional and/or alternative data sources 102 (e.g., one or more cloud computing platforms) that provide additional and/or alternative information to the enterprise computing platform 104.

In some variations, the data sources 102 may be implemented as engines, software functions, and/or applications. In other words, the functionalities of the data sources 102 may be implemented as software instructions stored in storage (e.g., memory) and executed by one or more processors.

The enterprise computing platform 104 is a computing platform that is associated with the enterprise organization. The enterprise organization may be any type of corporation, company, organization, and/or other institution. In some instances, the enterprise organization may own, operate, and/or be otherwise associated with a healthcare enterprise organization and/or an insurance institution. For instance, the enterprise organization may be associated with a medical provider that provides medical care and/or medical treatments for an individual. By using the care gap ML-AI models to predict care gaps for an individual, the enterprise organization may provide and/or perform preemptive actions to prevent exacerbation of the individual's medical conditions or worsening health as well as reduce the healthcare costs for its members.

As such, aspects of the present application may use ML-AI models to determine care gap information indicating probabilities of the individual opening or closing a care gap in the future.

For example, the enterprise computing platform 104 may train and/or use one or more care gap ML-AI models to determine care gap information. The care gap information may indicate probabilities for the individual opening a care gap and/or closing a care gap. A care gap may be a gap in time between when an individual (e.g., a member) was supposed to receive care for their medical condition and how long they have gone without care. For example, a member may have diabetes and may need to see a medical provider such as a doctor every six months. After seeing the doctor initially, the member may have a gap in care and might not have seen the doctor for ten months after their initial visit. As such, the care gap has been opened for four months (e.g., 10−6=4). A care gap intervention may be and/or include one or more care interventions that are used for individuals to manage their medical conditions (e.g., chronic/chronic-acute conditions). For instance, a care gap intervention may include displaying the care gap information on a computing device (e.g., on the care management computing device 108 and/or on a computing device associated with the enterprise computing platform 104). Additionally, and/or alternatively, the care gap intervention may further include automated phone calls to the individual indicating for the individual to see their medical provider and close their care gap and/or manual phone calls to the individual (e.g., the individual may be included in a list, and an operator may call the individuals on that list to inform the individuals to see their medical provider and close their care gap). Additionally, and/or alternatively, the care gap intervention may further include providing a physical letter, fax, or electronic delivery (e.g., email) to the medical provider of the individual or the individual themselves. Additionally, and/or alternatively, the care gap intervention may further include providing an alert to the care management computing device 108 and/or another computing device associated with care management for the individual. For instance, the alert may indicate for a person (e.g., a nurse) to address the open care gap of the individual.

The enterprise computing platform 104 includes one or more computing devices, computing platforms, systems, servers, and/or other apparatuses capable of performing tasks, functions, and/or other actions for the enterprise organization. For instance, the enterprise computing platform 104 may include the training system 110 that is configured to train the one or more care gap ML-AI models. The enterprise computing platform 104 may further include the prediction system 112 that is configured to use the trained care gap ML-AI models to determine the care gap information. In some variations, the enterprise computing platform 104 may be implemented as engines, software functions, and/or applications. In other words, the functionalities of the enterprise computing platform 104 may be implemented as software instructions stored in storage (e.g., memory) and executed by one or more processors.

The care management computing device 108 may be and/or include, but is not limited to, a desktop, laptop, tablet, mobile device (e.g., smartphone device, or other mobile device), smart watch, an internet of things (JOT) device, or any other type of computing device that generally comprises one or more communication components, one or more processing components, and one or more memory components. The care management computing device 108 may be able to execute software applications managed by, in communication with, and/or otherwise associated with the enterprise organization. Additionally, and/or alternatively, the care management computing device 108 may be configured to perform other functions.

In operation, the enterprise computing platform 104 may obtain information associated with a plurality of individuals (e.g., members) from the data sources 102. The enterprise computing platform 104 (e.g., the training system 110) may train one or more care gap ML-AI models using the obtained information. In some instances, the enterprise computing platform 104 may train a single care gap ML-AI model for each medical condition (e.g., each chronic condition). For instance, the enterprise computing platform 104 may filter the obtained information to determine information associated with individual's having a particular medical condition such as diabetes or a particular cardiovascular disease. The enterprise computing platform 104 may train the care gap ML-AI model based on the filtered information. For instance, the diabetes care gap ML-AI model may be trained using the information from individuals that have diabetes. Additionally, and/or alternatively, the enterprise computing platform 104 may further filter the information such as by filtering based on a business segment such as whether the individuals are under Medicare, Medicaid, commercial (e.g., individuals who have insurance that are not covered by Medicare), and/or by other filters (e.g., whether the individuals are fully insured or self-insured). Afterwards, the enterprise computing platform 104 may train the care gap ML-AI models. For example, the enterprise computing platform 104 may train a first care gap ML-AI model for diabetes and a second care gap ML-AI model for atherosclerotic cardiovascular disease. Additionally, and/or alternatively, the enterprise computing platform 104 may train multiple care gap ML-AI models for a single medical condition. For instance, the enterprise computing platform 104 may train two care gap ML-AI models for diabetes—a first care gap ML-AI model for Medicare and a second ML-AI model for commercial.

After training, the enterprise computing platform 104 (e.g., the prediction system 112) may determine care gap information for an individual using the trained care gap ML-AI model. For example, the enterprise computing platform 104 may receive individual information for the individual. The individual information may include one or more medical conditions of the individual (e.g., the individual has diabetes) and personal information of the individual. The enterprise computing platform 104 may determine the care gap information using the individual information and the trained ML-AI model. The care gap information indicates one or more predictions for the expectancy of a care gap of the individual. For example, the care gap information may indicate probabilities that the care gap of the individual will close or open within a certain time period such as within the next twelve months. Based on the care gap information, the enterprise computing platform 104 may perform one or more care gap interventions.

For example, the enterprise computing platform 104 may determine that a first individual has an 84% chance of closing their care gap by six months and a second individual has a 64% chance. As such, the enterprise computing platform 104 may perform a care gap intervention by prioritizing the second individual. For instance, the enterprise organization may employ a certain number of employees to make phone calls to the individuals to inform them that they should be closing their care gap. However, with the number of employees, it may be difficult to contact every individual with an open care gap. Accordingly, the enterprise computing platform 104 may use the care gap ML-AI models to better allocate resources and prioritize individuals to increase care gap closures. For instance, the enterprise computing platform 104 may generate a list based on the care gap information for a plurality of individuals. For example, the enterprise computing platform 104 may include individuals with below a 75% chance of closing their care gap onto the list. As such, the second individual is included on the list whereas the first individual is not. Then, the enterprise computing platform 104 may perform an action based on that list. For instance, the enterprise computing platform 104 may provide the list to the care management computing device 108. The care management computing device 108 may display information indicating the list, and the employees of the enterprise organization may call or otherwise contact the individuals based on the displayed information. Additionally, and/or alternatively, the care management computing device 108 may include an automated telephone and/or messaging service. The care management computing device 108 may automatically call or message (e.g., text, email, via an application messaging system, etc.) individuals on the list after receiving the list from the enterprise computing platform 104.

In some instances, the enterprise computing platform 104 may determine that a first individual has a 30% chance of closing the care gap at month one, but a non-changing 80% chance by month three and onwards. The enterprise computing platform 104 may further determine that a second member has a 50% chance of closing the care gap at month one and a 60% chance by month three and onwards. In such instances, the enterprise computing platform 104 may target the second individual, but may also target the first individual based on one or more threshold values and/or other processes that the enterprise computing platform 104 may perform. Therefore, by using the care gap ML-AI models, a more informed manner to choose who to target for care gap interventions can be performed, which will increase care gap closures through such interventions.

In some variations, as mentioned above, each care gap ML-AI model may be associated with a particular medical condition such as diabetes. Based on the medical condition of the individual, the enterprise computing platform 104 may select (e.g., determine) a care gap ML-AI model from a plurality of care gap ML-AI models, and use the selected care gap ML-AI model to determine the care gap information for the individual. Additionally, and/or alternatively, the enterprise computing platform 104 may determine whether the individual is commercial or Medicare, and then determine the appropriate care gap ML-AI model based on whether the individual is commercial or Medicare and/or the medical condition of the individual.

In some examples, the care gap ML-AI models may be and/or include closed care gap ML-AI models. For instance, the care gap information that is output from the closed care gap ML-AI models may indicate probabilities for likelihood that the individual with a currently open care gap will close their care gap. For example, after seeing the medical provider, the next medical visit may be scheduled for six months in the future. If the individual sees the medical provider at that scheduled six month date, he/she has received his/her care and no care gap is opened. However, if the individual does not see the medical provider at that scheduled six month date, then he/she has missed her scheduled care and a care gap will have begun to form. The enterprise computing platform 104 may use the closed care gap ML-AI models to determine the probabilities indicating the likelihood that the individual will close their care gap after it has been opened. For instance, the enterprise computing platform 104 may determine for a given individual identified in the database at the point in time with an open care gap, the first probability of closure in a subsequent first month, a second probability for a second month, a third probability for a third month, a fourth probability for a fourth month and so on. Each probability may indicate the likelihood that the individual will close their care gap in the given month (e.g., the second probability may indicate the likelihood that the individual will close their care gap in the second month). The enterprise computing platform 104 may perform one or more care gap interventions (e.g., providing instructions to the care management computing device 108 to provide an automated call to the individual) based on the care gap information from the closed care gap ML-AI Model such as the second probability indicating the likelihood that the individual will close their care gap in that month.

In some instances, the care gap ML-AI models may be and/or include open care gap ML-AI models. In contrast to closed care gap ML-AI models, the open care gap ML-AI models may provide care gap information indicating probabilities for the likelihood that the individual with a closed (thus not open) care gap will open up a care gap within a certain time period. For instance, the enterprise computing platform 104 may determine for a given individual identified in the database with a closed care gap a first probability for the subsequent first month indicating the likelihood that a care gap for the individual will open, a second probability for a second month indicating the likelihood that a care gap for the individual will open, and so on.

In some variations, the enterprise computing platform 104 may perform data manipulation and/or cleaning prior to using the data to the train the one or more care gap ML-AI models. For instance, the enterprise computing platform 104 may perform outlier removal, removal of nulls, and/or feature filtration prior to training the care gap ML-AI models. This and other examples will be described in further detail below.

It will be appreciated that the exemplary environment depicted in FIG. 1 is merely an example, and that the principles discussed herein may also be applicable to other situations—for example, including other types of institutions, organizations, devices, systems, and network configurations. As will be described herein, the environment 100 may be used by health care enterprise organizations. However, in other instances, the environment 100 may be used by other types of enterprise organizations such as financial institutions or insurance institutions.

Figure 2:
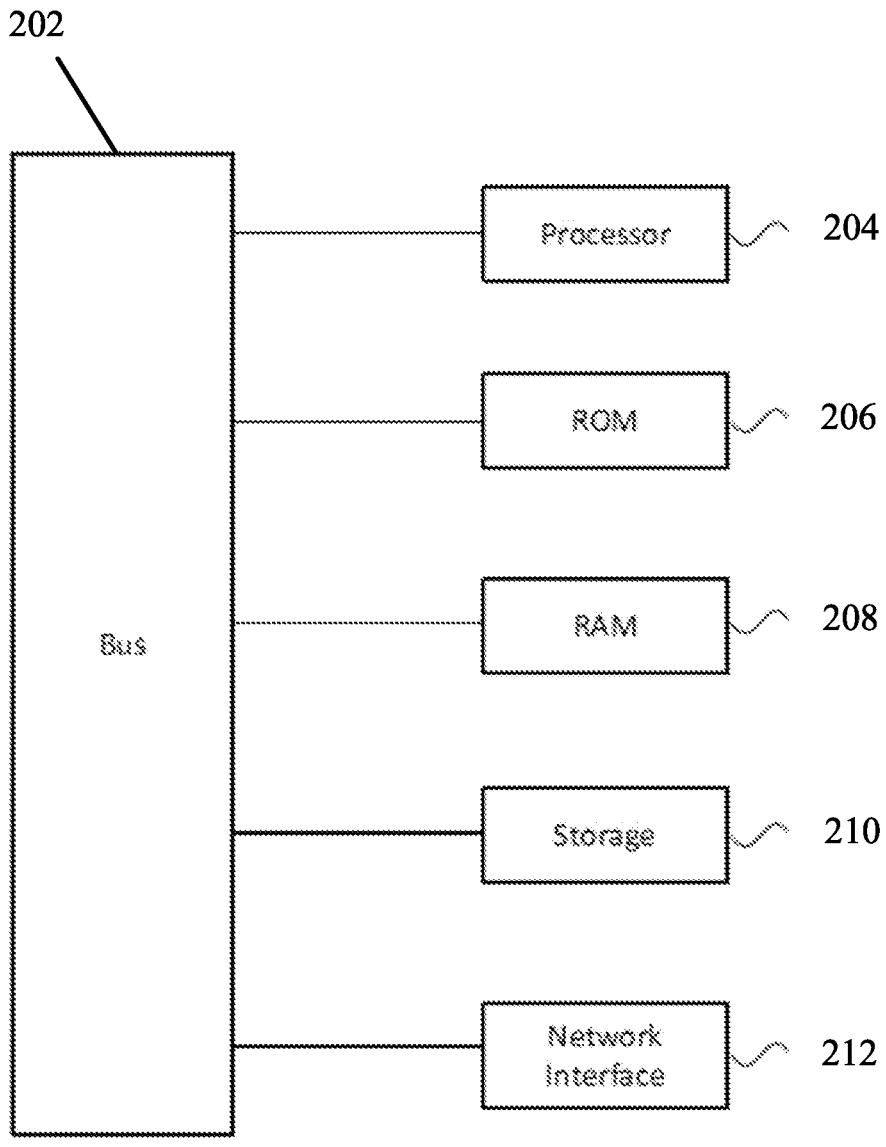
FIG. 2 is a simplified block diagram of one or more devices or systems within the exemplary environment of FIG. 1.

FIG. 2 is a block diagram of an exemplary system and/or device 200 within the environment 100. The device/system 200 includes a processor 204, such as a central processing unit (CPU), controller, and/or logic, that executes computer executable instructions for performing the functions, processes, and/or methods described herein. In some examples, the computer executable instructions are locally stored and accessed from a non-transitory computer readable medium, such as storage 210, which may be a hard drive or flash drive. Read Only Memory (ROM) 206 includes computer executable instructions for initializing the processor 204, while the random-access memory (RAM) 208 is the main memory for loading and processing instructions executed by the processor 204. The network interface 212 may connect to a wired network or cellular network and to a local area network or wide area network, such as the network 106. The device/system 200 may also include a bus 202 that connects the processor 204, ROM 206, RAM 208, storage 210, and/or the network interface 212. The components within the device/system 200 may use the bus 202 to communicate with each other. The components within the device/system 200 are merely exemplary and might not be inclusive of every component within the device/system 200.

FIG. 3 is an exemplary process 300 for using the care gap ML-AI model to identify care gaps. The process 300 may be performed by the enterprise computing platform 104 shown in FIG. 1. However, it will be recognized that any of the following blocks may be performed in any suitable order and that the process 300 may be performed in any suitable environment. The descriptions, illustrations, and processes of FIG. 3 are merely exemplary and the process 300 may use other descriptions, illustrations, and processes.

At block 302, the enterprise computing platform 104 obtains (e.g., receives, determines, generates, and/or trains) one or more care gap ML-AI models. For instance, the enterprise computing platform 104 (e.g., the training system 110) may first train the one or more care gap ML-AI models prior to using the one or more care gap ML-AI models. For example, the enterprise computing platform 104 may receive information (e.g., population information) for a plurality of individuals from the data sources 102. Based on the received information, the enterprise computing platform 104 may determine one or more features, and the features may be used to train the one or more care gap ML-AI models.

The enterprise computing platform 104 may determine modeling data based on information received from the data sources 102 (e.g., gap status tables from the CSID and/or other information from the other data sources 102). For instance, in some variations, the modeling data may include information indicating individuals with an open gap at the beginning of a target period for each medical condition (e.g., each chronic medical condition). The enterprise computing platform 104 may determine the features based on a time period (e.g., twelve months) prior to the first month's target period, and the prediction target may be derived from twelve months post the first month of the target period. As such, the care gap ML-AI models may support gap survival predictions of up to twelve months. In other words, during model training and using the most recently available data, the enterprise computing platform 104 may train a care gap ML-AI model using feature data (e.g., data from January 2019 to December 2019) and target data (e.g., data from January 2020 and December 2020. For example, the enterprise computing platform may use the feature data to actually train the care gap ML-AI model, and use the target data to score the trained care gap ML-AI model and determine whether it is sufficiently trained. Afterwards, each care gap ML-AI model may provide care gap information (e.g., monthly care gap closure probabilities) for the subsequent twelve months from January 2021 to December 2021. The dates provided above are merely examples, and the enterprise computing platform 104 may use different dates for the feature data and target data to train and score the care gap ML-AI models, as well as to predict the care gap information for the subsequent twelve months.

In some instances, the enterprise computing platform 104 may determine a plurality of features based on the information received from the data sources 102. For instance, the enterprise computing platform 104 may determine modeling data indicating the plurality of features. The plurality of features include, but are not limited to, gender of the individual, age of the individual, medical coverage of the individual (e.g., whether the individual has medical coverage/insurance), prescription coverage of the individual (e.g., whether the individual has coverage for prescriptions), total procedure event count during the feature period (e.g., the number of medical procedures the individual has undergone during a time period), total lab event count during the feature period (e.g., the amount of lab work associated with an individual during a time period), total drug event count during the feature period, one or more medical and/or risk scores (e.g., using one or more models, algorithms, and/or ML-AI models to determine scores associated with the individual), average open period (e.g., average amount of time a given individual has had open care gaps), average closed period (e.g., average amount of time a given individual has had closed care gaps), buyer presence of an automobile (e.g., indicator as to whether the individual has access to an automobile), county or national income percentile (e.g., what percentile the individual's income is at compared to others in their county or compared to others on a national level), estimated income (e.g., estimated household income), total property value lower bound (e.g., lowest value of the property value for the individual within a time period), length of residence at current domicile, likelihood of the individual using a loyalty card, likelihood of individual purchasing food and/or beverage category (e.g., likelihood of individual purchasing certain foods or beverages), education attainment of the individual, and so on.

In some examples, the modeling data may indicate the features for the plurality of individuals. For instance, the modeling data may be and/or include one or more arrays with the features being in the columns and the rows indicating the plurality of individuals. Additionally, and/or alternatively, the enterprise computing platform 104 may generate a plurality of care gap ML-AI models, and each of the care gap ML-AI models may be associated with a medical condition. As such, the enterprise computing platform 104 may filter the modeling data based on the medical condition (e.g., diabetes), and use the filtered modeling data to train the care gap ML-AI model for the particular medical condition (e.g., diabetes).

Additionally, and/or alternatively, a subset of the care gap ML-AI models from the plurality of care gap ML-AI models may be associated with a particular medical condition. For instance, the care gap ML-AI models for the particular medical condition may include a first care gap ML-AI model for commercial and a second care gap ML-AI model for Medicare. Additionally, and/or alternatively, each of the subset of the care gap ML-AI models for a particular medical condition may be associated with one or more population cohorts (e.g., care gap cohorts). The population cohorts may be different for closed care gap ML-AI models and open care gap ML-AI models. For example, for closed care gap ML-AI models, the population or care gap cohorts are defined and grouped based on a number of months of existing open care gaps. For instance, the individuals with a one month open care gap may be grouped together as a first care gap cohort, individuals with a two month open care gap may be grouped together as a second care gap cohort, individuals with a three month open care gap may be grouped together as a third care gap cohort, and so on. For open care gap ML-AI models, the population or care gap cohorts are defined and grouped based on a number of months of existing closed care gaps. For example, the individuals with a one month closed care gap may be grouped together as a first care gap cohort, individuals with a two month closed care gap may be grouped together as a second care gap cohort, individuals with a three month closed care gap may be grouped together as a third care gap cohort, and so on.

In some instances, the enterprise computing platform 104 may filter the modeling data for a plurality of care gap cohorts (e.g., twelve care gap cohorts for the next twelve month period). For instance, the enterprise computing platform 104 may filter the modeling data for the first care gap cohort (e.g., for closed care gap ML-AI models, the enterprise computing platform 104 may filter out the modeling data based on individuals that have a one month open care gap, and have the same medical condition such as diabetes). The enterprise computing platform 104 may filter the modeling data for the second care gap cohort, and so on. Afterwards, the enterprise computing platform 104 may train a subset of care gap ML-AI models for the medical condition based on the filtered modeling data and the care gap cohort. For instance, if there are twelve care gap cohorts, the enterprise computing platform 104 may train twelve separate care gap ML-AI models. In some instances, one or more care gap cohorts might not have enough modeling data to train the care gap ML-AI model. In such instances, the enterprise computing platform 104 may group two or more of the cohorts together (e.g., the first through fourth care gap cohorts, fifth through eighth care gap cohorts, and ninth through twelfth care gap cohorts), and train one care gap ML-AI model for each group (e.g., a first ML-AI model for first through fourth, a second ML-AI model for fifth through eighth, and a third ML-AI model for ninth through twelfth). Afterwards, each care gap ML-AI model may provide care gap information (e.g., monthly care gap closure probabilities) for a certain time period (e.g., the next twelve months).

Accordingly, the enterprise computing platform 104 may train one or more care gap ML-AI models for the one or more medical conditions (e.g., a single care gap ML-AI model for the medical condition or multiple care gap ML-AI models for the medical condition).

The care gap ML-AI models may be any type of ML-AI model (e.g., unsupervised, supervised, and/or deep learning) that can be used to determine the care gap information. For instance, the care gap ML-AI model may be a survival analysis model. In some instances, the care gap ML-AI model may be gradient boosting machine (GBM), logistic regression, and/or other types of ML-AI models.

In some variations, prior to training the care gap ML-AI models, the enterprise computing platform 104 may perform data manipulation and/or cleaning of the modeling data. For instance, the enterprise computing platform 104 may perform outlier removal. For example, the enterprise computing platform 104 may first fit a baseline survival model and check the deviance residuals of the model fit. The enterprise computing platform 104 may determine data points as outliers if their deviance residuals are within the bottom 5% or top 5% quantile (by default 10% outliers, but different values may also be used by the enterprise computing platform 104). The enterprise computing platform 104 may remove these outliers from the modeling data prior to training the care gap ML-AI model. In some instances, these outliers may still be used by the enterprise computing platform 104 when the training set ends up with only one event class (all closed or all open gaps) in the target class distribution data after removing the outliers during the training process for the care gap ML-AI models. In other words, in some examples, if there is a completely homogenous class distribution with only one class (e.g., only individuals with open care gaps) in the target data, then it could cause the training for the care gap ML-AI models to become difficult (e.g., it may be difficult to predict a probability of closure if there is no data to build it out in the first place). In such examples, the enterprise computing platform 104 may still use these determined outliers for training of the care gap ML-AI models.

Additionally, and/or alternatively, the enterprise computing platform 104 may perform removal of nulls. For instance, the enterprise computing platform 104 may remove null values when merging feature tables together. Any remaining null values that may arise are imputed with 0's. This may be performed to enrich the quality of the modeling data as much as possible while removing an immaterial number of data point from the modeling data.

Additionally, and/or alternatively, the enterprise computing platform 104 may perform feature filtration. For instance, the enterprise computing platform 104 may apply a variance threshold (e.g., default threshold is set to 0.01) to every candidate feature in the modeling dataset. This is done to remove insignificant features and reduce data dimensionality. Having homogenous features might not yield any model sensitivities to differing dependent variable fluctuations.

In some instances, after filtering, cleaning, selecting, and/or otherwise manipulating or modifying the modeling data, the enterprise computing platform 104 may train the care gap ML-AI model (e.g., train the care gap ML-AT model for a particular condition, cohort, business segment such as commercial or Medicare, and/or other examples described above). For instance, the enterprise computing platform 104 may split the data into training data and test data. Then, the enterprise computing platform 104 may train the care gap ML-AI model using the training data to predict the test data as best as possible. For example, the enterprise computing platform 104 may train the ML-AI model by determining whether the training data is continuous or discrete and/or using one or more regression/classification algorithms. After training the ML-AI model, the enterprise computing platform 104 may test the trained model on the test data. The enterprise computing platform 104 may perform another continuous or discrete analysis and render a decision whether to proceed with the current ML-AI model or retrain a new one with differing parameters based on model performance metrics and/or other potential factors.

After training the care gap ML-AI models, the enterprise computing platform 104 may store and/or use the care gap ML-AI models. In some instances, the training system 110 may train the care gap ML-AI models and store them in memory (e.g., a database). The prediction system 112 may obtain (e.g., receive and/or retrieve) the care gap ML-AI models from memory.

At block 304, the enterprise computing platform 104 (e.g., the prediction system 112) obtains individual information of an individual comprising one or more medical conditions of the individual and personal information of the individual. For instance, the medical condition of the individual may indicate one or more chronic medical conditions that the individual has (e.g., diabetes or cardiovascular disease. The personal information may indicate one or more of the features described above. In some instances, after the removal of the nulls, the personal information may be a matrix with the features as the different column headings, and the columns being populated with information associated with the individuals.

At block 306, the enterprise computing platform 104 determines care gap information of the individual based on using the one or more care gap ML-AI models and the individual information. The care gap information indicates one or more predictions for expectancy of a care gap of the individual. The care gap is associated with a gap in time that the individual has a lapse in receiving medical care for the one or more medical conditions.

For example, the enterprise computing platform 104 may first select a care gap ML-AI model to use for the individual. For instance, based on the medical condition of the individual, the enterprise computing platform 104 may select a care gap ML-AI model associated with the medical condition. Additionally, and/or alternatively, the enterprise computing platform 104 may select the care gap ML-AI model based on the medical condition, the business segment (e.g., commercial or Medicare) of the individual, and/or the care gap cohort of the individual (e.g., how long the individual has gone without seeing the medical provider, a gap in time that the individual has a lapse in receiving medical care for their medical condition, or a length of time that the individual does not have a care gap). For example, the individual information may indicate that the individual has diabetes and for the individual to see their medical provider every six months. It might be eight months since the individual has seen their medical provider. As such, the care gap cohort (e.g., closed care gap cohort) of the individual may be two months. Therefore, the enterprise computing platform 104 may select the care gap ML-AI model for diabetes with a care gap cohort of two months. In other words, in some examples, the enterprise computing platform 104 may perform a comparison between the characteristics of the individual (e.g., the medical condition, the business segment, the care gap cohort of the individual) and the characteristics associated with each of the care gap ML-AI models (e.g., the filtered modeling data that was used to train each of the care gap ML-AI models such as the filtered modeling data for diabetes and/or for a first care gap cohort). Based on the comparison, the enterprise computing platform 104 may select a care gap ML-AI model (e.g., a closed care gap ML-AI model) to use for the individual.

For the open care gap ML-AI models, the enterprise computing platform 104 may select the care gap ML-AI model based on performing a comparison between characteristics of the individual and the characteristics associated with each of the open care gap ML-AI models. For instance, the enterprise computing platform 104 may perform a comparison between the characteristics of the individual (e.g., the medical condition, the business segment, the care gap cohort of the individual) and the characteristics associated with each of the open care gap ML-AI models (e.g., the filtered modeling data that was used to train each of the open care gap ML-AI models such as the filtered modeling data for diabetes and/or for a first care gap cohort). Based on the comparison, the enterprise computing platform 104 may select an open care gap ML-AI model to use for the individual. For instance, the enterprise computing platform 104 may compare a length of time that the individual has accumulated a closed care gap (e.g., a duration that the care gap of the individual has been closed for) with the care gap cohort associated with the care gap ML-AI models. For example, based on the individual having a care gap that has been closed for three months, the enterprise computing platform 104 may select the open care gap ML-AI model with an open care gap cohort of three months.

After selecting the care gap ML-AI model, the enterprise computing platform 104 may use the care gap ML-AI model to determine the care gap information. For instance, the enterprise computing platform 104 may input information associated with the individual information into the selected care gap ML-AI model. The enterprise computing platform 104 may obtain model output indicating the care gap information of the individual. For instance, the care gap information of the individual may indicate a plurality of probabilities indicating the likelihood that the individual will close or open the care gap within a certain time period in the future (e.g., the next twelve months).

FIG. 5 shows exemplary care gap information based on using the care gap ML-AI model in accordance with one or more examples of the present application, and will be used to describe block 306 in more detail. For instance, the care gap information 500 for five members ("Member A" through "Member E") are shown. The top row shows the time period for the care gap (e.g., month 1 to month 12). Within each entry of the care gap information 500 includes probabilities indicating likelihood for opening or closing the care gap. For example, by using a closed care gap ML-AI model, the care gap information 500 may indicate probabilities for each of the members over a twelve month period that the member will close their care gap by that specific time span. For example, for "Member A", this member has a 13.9% chance of closing their care gap in the first month, and the probability gradually increases to 26.0% in month two, 38.6% in month three, all the way to 84.1% in month twelve. As such, the member has a 13.9% chance to close their care gap in the first month, a 26% chance to close their care gap by month two (e.g., in the first month or in the second month), a 38.6% chance to close their care gap by month three (e.g., in the first month, the second month, or the third month), and so on. Similarly, for "Member C", this member has a 13.0% chance of closing their care gap in the first month, 24.5% chance in month two, and this goes to 82.1% in month twelve. In some instances, the care gap information 500 may be associated with individuals with a closed care gap cohort of two months. For instance, the individuals may have an open care gap of two months. Thus, after using the selected closed care gap ML-AI model, the enterprise computing platform 104 may determine the care gap information 500. Therefore, for month one shown in FIG. 5, the care gap information 500 indicates 13.9% likelihood that Member A will close their care gap in the next month (e.g., in the third month since the care gap has opened). Similarly, the care gap information 500 indicates a 26.0% chance that Member A will close their care gap in the next two months (e.g., in the third or fourth month since the care gap has opened).

In other instances, the enterprise computing platform 104 may provide care gap information that is associated with individuals with an open care gap cohort of five months. For example, the individuals may have a closed care gap of five months. Thus, after using the selected open care gap ML-AI model, the enterprise computing platform 104 may determine the care gap information. Therefore, for month one, the care gap information indicates a first probability that Member A will open their care gap in the next month (e.g., in the sixth month since the care gap has been closed). Similarly, the care gap information indicates a second probability that Member A will open their care gap in the next two months (e.g., in the sixth or seventh month since the care gap has been closed), and so on.

In some instances, the enterprise computing platform 104 may use survival analysis as the care gap ML-AI model to generate the care gap information 500. The survival analysis utilizes a predetermined function (e.g., KAPLAN-MEIER, COX PROPORTIONAL HAZARD) to estimate the conditional probabilities of survival from time t=0 to the end of the event (e.g., a care gap closure such as the individual visiting their medical provider for a check-up on their medical condition). As shown in FIG. 5, the table indicating the care gap information 500 is provided at a member level, with each row thus representing the probability of closure for each ascending month over a twelve-month time period. As shown, as time passes, the probability that a member will close their care gap increases, which is described above.

At block 308, the enterprise computing platform 104 performs one or more care gap interventions based on the care gap information. For example, the enterprise computing platform 104 may compare entries from the care gap information with one or more thresholds and/or other metrics. Based on the comparison, the enterprise computing platform 104 may perform (e.g., actually perform and/or facilitate the performance of) one or more care gap interventions such as providing one or more instructions or commands to the care management computing device 108. For example, the enterprise computing platform 104 may provide instructions to the care management computing device 108 to display a prompt indicating for an operator to contact (e.g., via email, letter, fax, or phone) the individual and/or the medical provider for the individual so as to address their care gap. Additionally, and/or alternatively, the care management computing device 108 may provide automated emails, telephone calls, or other automated contact methods to the individual and/or the medical provider for the individual based on instructions from the enterprise computing platform 104. Additionally, and/or alternatively, the enterprise computing platform 104 may provide an alert to the care management computing device 108 and/or another computing device associated with the care management for the individual. The alert may indicate for a person (e.g., nurse) associated with care management for the individual to contact the individual so that the individual can address the care gap.

Figure 4:
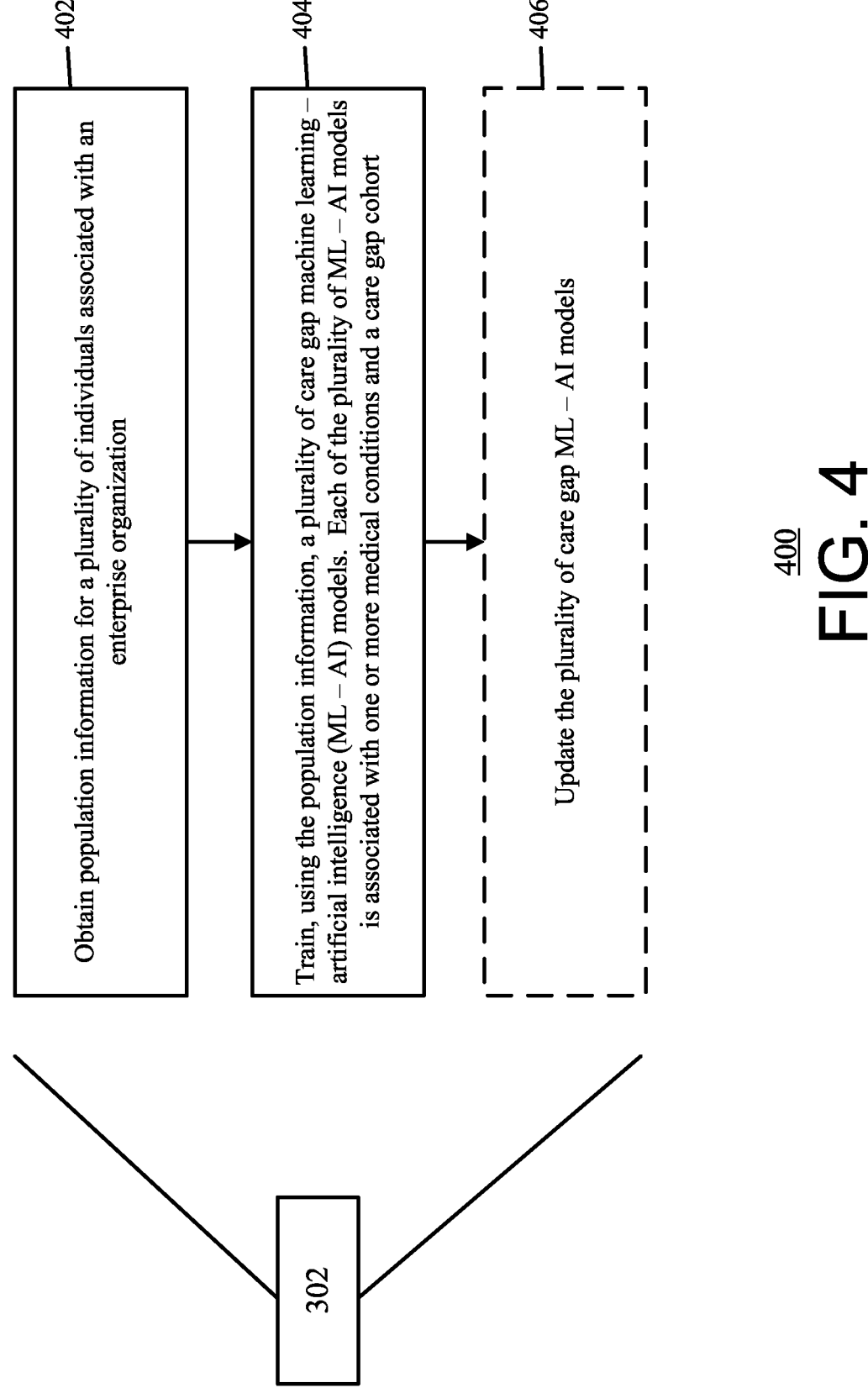
FIG. 4 is another exemplary process for using the care gap ML-AI model to identify care gaps in accordance with one or more examples of the present application.

FIG. 4 is another exemplary process for using the care gap ML-AI model to identify care gaps in accordance with one or more examples of the present application. FIG. 4 describes block 302 of process 300 in more detail. For instance, FIG. 4 shows a process 400 that may be used by the enterprise computing platform 104 to train the care gap ML-AI models. The process 400 may be performed by the enterprise computing platform 104 (e.g., the training system 110) shown in FIG. 1. However, it will be recognized that any of the following blocks may be performed in any suitable order and that the process may be performed in any suitable environment. The descriptions, illustrations, and processes of FIG. 4 are merely exemplary and the process may use other descriptions, illustrations, and processes.

At block 402, the enterprise computing platform 104 obtains population information for a plurality of individuals associated with an enterprise organization. The population information may indicate the features described above that are used to train the care gap ML-AI models.

At block 404, the enterprise computing platform 104 trains, using the population information (e.g., the features), a plurality of care gap ML-AI models. Each of the plurality of ML-AI models is associated with one or more medical conditions and a care gap cohort. For example, as mentioned above, the enterprise computing platform 104 may modify the population information, and train the care gap ML-AI models based on the modified population information. For instance, the enterprise computing platform 104 may perform filtering of the population information based on the medical conditions, the care gap cohorts, and/or other filtering criteria (e.g., business segment). Additionally, and/or alternatively, the enterprise computing platform 104 may perform data manipulation and/or cleaning such as removal of nulls or outliers.

Afterwards, the enterprise computing platform 104 may use the trained care gap ML-AI models. Additionally, and/or alternatively, the enterprise computing platform 104 may update the plurality of care gap ML-AI models. Block 406 is in a dotted line to denote that it is optional. When performed, the enterprise computing platform 104 updates the plurality of care gap ML-AI models. For instance, the population information may change every so often (e.g., every month). Therefore, in some variations, at block 406, the enterprise computing platform 104 may update the care gap ML-AI models every month. For instance, the enterprise computing platform 104 may receive or obtain new data from the data sources 102 periodically (e.g., every month). Then, the enterprise computing platform 104 may train new care gap ML-AI models and/or update previously trained care gap ML-AI models periodically. For instance, the enterprise computing platform 104 may pull the previous twelve months of features/targets to create the modeling data, and train the care gap ML-AI models. In some examples, the enterprise computing platform 104 may update the care gap ML-AI models based on a trigger. For instance, the trigger may be to update the care gap ML-AI models at a periodic interval (e.g., every month). Additionally, and/or alternatively, the trigger may be a user input indicating to update the care gap ML-AI models.

Additionally, and/or alternatively, the enterprise computing platform 104 may determine performance metrics for the trained care gap ML-AI models. For instance, the enterprise computing platform 104 may pull twelve months of features for the current members to create a scoring table. The enterprise computing platform 104 may predict twelve months gap survival probability using the trained care gap ML-AI models and store the prediction as hive tables on production.

In some instances, the enterprise computing platform 104 may train twenty-four care gap ML-AI models for each medical condition. For instance, the twenty four care gap ML-AI Models may include twelve care gap ML-AI models for Medicare and twelve for commercial. Further, each of the twelve care gap ML-AI models may be for each care gap cohort (e.g., month one through month twelve).

In some instances, the enterprise computing platform 104 may train care gap ML-AI models for medical conditions such as, but not limited to, heart failure, diabetes, coronary artery disease, individuals on non-steroidal anti-inflammatory drugs (NSAIDs), hyperkalemia, hypertension, chronic kidney disease, asthma, atherosclerotic cardiovascular disease, pregnancy, chronic obstructive pulmonary disease (COPD), individuals on chronic opioid therapy, major depression, and/or other medical conditions.

Figure 6:
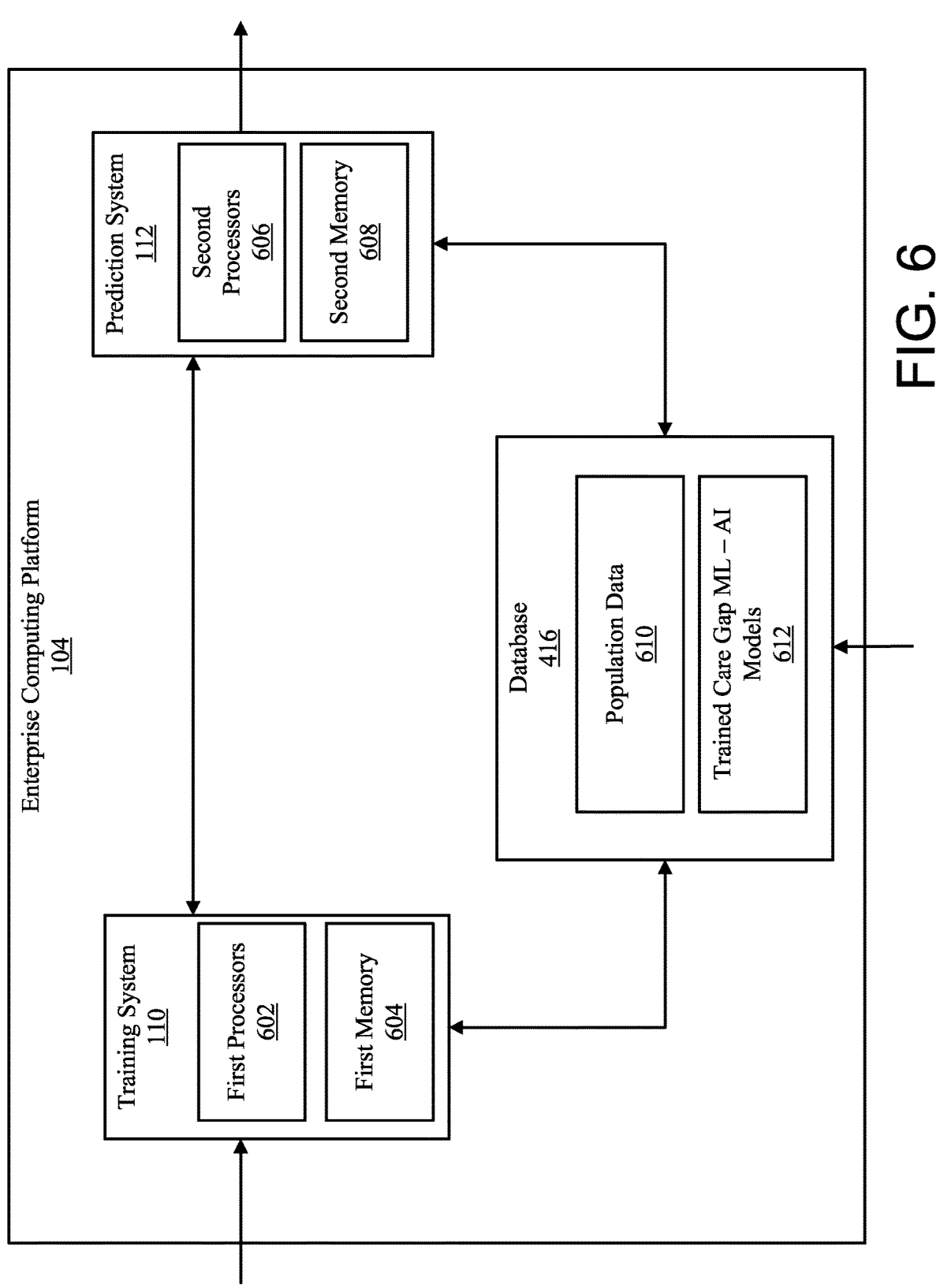
FIG. 6 is a simplified block diagram depicting an exemplary enterprise computing platform in accordance with one or more examples of the present application.

FIG. 6 is a simplified block diagram depicting an exemplary enterprise computing platform in accordance with one or more examples of the present application. For instance, the enterprise computing platform 104 includes the training system 110, the prediction system 112, and a database 416.

For instance, the database 416 may store the population data 610 and the trained care gap ML-AI models. The training system 110 may include first processors 602 and first memory 604. The training system 110 may be configured to train the care gap ML-AI models as described above. The prediction system 112 may include second processors 606 and second memory 608. The prediction system 112 may be configured to use the trained care gap ML-AI models to determine care gap information.

A number of implementations have been described. Nevertheless, it will be understood that additional modifications may be made without departing from the scope of the inventive concepts described herein, and, accordingly, other examples are within the scope of the following claims. For example, it will be appreciated that the examples of the application described herein are merely exemplary. Variations of these examples may become apparent to those of ordinary skill in the art upon reading the foregoing description. The inventor expects skilled artisans to employ such variations as appropriate, and the inventor intends for the application to be practiced otherwise than as specifically described herein. Accordingly, this application includes all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

It will further be appreciated by those of skill in the art that the execution of the various machine-implemented processes and steps described herein may occur via the computerized execution of processor-executable instructions stored on a non-transitory computer-readable medium, e.g., random access memory (RAM), read-only memory (ROM), programmable read-only memory (PROM), volatile, nonvolatile, or other electronic memory mechanism. Thus, for example, the operations described herein as being performed by computing devices and/or components thereof may be carried out by according to processor-executable instructions and/or installed applications corresponding to software, firmware, and/or computer hardware.

The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the application and does not pose a limitation on the scope of the application unless otherwise claimed. No language in the specification should be construed as indicating any non-claimed element as essential to the practice of the application.

The invention claimed is:

1. A method, comprising:

obtaining population information for a plurality of individuals associated with an enterprise organization;

filtering the population information using a plurality of care gap cohorts to determine a subset of the population information for each of the plurality of care gap cohorts;

training a plurality of care gap machine learning-artificial intelligence (ML-AI) models based on the subset of the population information such that each of the plurality of care gap ML-AI models is associated with one or more care gap cohorts from the plurality of care gap cohorts;

determining to retrain a first care gap ML-AI model, of the plurality of care gap ML-AI models, based on a first care gap cohort, of the plurality of care gap cohorts, having insufficient data to train the first care gap ML-AI model;

based on the determination, combining a first subset of the population information associated with the first care gap cohort with a second subset of the population information associated with a second care gap cohort from the plurality of care gap cohorts to obtain combined population information;

retraining the first care gap ML-AI model based on the combined population information;

obtaining individual information of an individual, wherein the individual information indicates one or more medical conditions of the individual and a care gap of the individual indicating a gap in time that the individual has a lapse in receiving medical care for the one or more medical conditions;

selecting the first care gap ML-AI model, from the plurality of care gap ML-AI models, based on comparing the gap in time that the individual has the lapse in receiving medical care for the one or more medical conditions with the plurality of care gap cohorts;

determining care gap information of the individual based on using the first care gap ML-AI model and the individual information; and performing one or more care gap interventions based on the care gap information.

2. The method of claim 1, wherein each of the plurality of care gap ML-AI models is further associated with a particular medical condition, and wherein selecting the first care gap ML-AI model is further based on comparing the one or more medical conditions of the individual with the particular medical condition associated with each of the plurality of care gap ML-AI models.

3. The method of claim 1, wherein the plurality of care gap ML-AI models are a plurality of closed care gap ML-AI models associated with probabilities that individuals with an open care gap will close the open care gap.

4. The method of claim 1, wherein selecting the first care gap ML-AI model is further based on the one or more medical conditions of the individual.

5. The method of claim 1, wherein the individual information of the individual indicates a business segment associated with the individual, and wherein selecting the first care gap ML-AI model is further based on the business segment associated with the individual.

6. The method of claim 1, wherein obtaining the individual information of the individual comprises:

receiving the individual information of the individual from an external source, wherein the individual information comprises financial information associated with the individual and prescription information of the individual.

7. The method of claim 1, wherein the first care gap ML-AI model is a closed care gap ML-AI model, and wherein performing the one or more care gap interventions based on the care gap information comprises:

displaying a plurality of probabilities indicating a likelihood of the individual closing the care gap within a time span.

8. The method of claim 1, wherein the first care gap ML-AI model is an open care gap ML-AI model, and wherein performing the one or more care gap interventions based on the care gap information comprises:

displaying a plurality of probabilities indicating a likelihood of the individual opening the care gap within a time span.

9. The method of claim 1, wherein determining to retrain the first care gap ML-AI model is based on a triggering event.

10. The method of claim 1, wherein filtering the population information is further based on a plurality of medical conditions.

11. The method of claim 1, wherein filtering the population information comprises:

performing data manipulation on the population information comprising removal of nulls, feature filtration, or outlier removal.

12. The method of claim 1, wherein the plurality of care gap ML-AI models comprises a survival analysis ML-AI model.

13. A computing platform, comprising:

one or more processors; and a non-transitory computer-readable medium having processor-executable instructions stored thereon, wherein the processor-executable instructions, when executed by the one or more processors, facilitate:

obtaining population information for a plurality of individuals associated with an enterprise organization;

filtering the population information using a plurality of care gap cohorts to determine a subset of the population information for each of the plurality of care gap cohorts;

training a plurality of care gap machine learning-artificial intelligence (ML-AI) models based on the subset of the population information such that each of the plurality of care gap ML-AI models is associated with one or more care gap cohorts from the plurality of care gap cohorts;

determining to retrain a first care gap ML-AI model, of the plurality of care gap ML-AI models, based on a first care gap cohort, of the plurality of care gap cohorts, having insufficient data to train the first care gap ML-AI model;

based on the determination, combining a first subset of the population information associated with the first care gap cohort with a second subset of the population information associated with a second care gap cohort from the plurality of care gap cohorts to obtain combined population information;

retraining the first care gap ML-AI model based on the combined population information;

obtaining individual information of an individual, wherein the individual information indicates one or more medical conditions of the individual and a care gap of the individual indicating a gap in time that the individual has a lapse in receiving medical care for the one or more medical conditions;

selecting the first care gap ML-AI model, from the plurality of care gap ML-AI models, based on comparing the gap in time that the individual has the lapse in receiving medical care for the one or more medical conditions with the plurality of care gap cohorts;

determining care gap information of the individual based on using the first care gap ML-AI model and the individual information; and performing one or more care gap interventions based on the care gap information.

14. The computing platform of claim 13, wherein each of the plurality of care gap ML-AI models is further associated with a particular medical condition, and wherein selecting the first care gap ML-AI model is further based on comparing the one or more medical conditions of the individual with the particular medical condition associated with each of the plurality of care gap ML-AI models.

15. The computing platform of claim 13, wherein the plurality of care gap ML-AI models are a plurality of closed care gap ML-AI models associated with probabilities that individuals with an open care gap will close the open care gap.

16. The computing platform of claim 13, wherein filtering the population information comprises:

performing data manipulation on the population information comprising removal of nulls, feature filtration, or outlier removal.

17. The computing platform of claim 13, wherein determining to retrain the first care gap ML-AI model is based on a triggering event.

18. The computing platform of claim 13, wherein the first care gap ML-AI model is a closed care gap ML-AI model, and wherein performing the one or more care gap interventions based on the care gap information comprises:

displaying a plurality of probabilities indicating a likelihood of the individual closing the care gap within a time span.

19. The computing platform of claim 13, wherein the first care gap ML-AI model is an open care gap ML-AI model, and wherein performing the one or more care gap interventions based on the care gap information comprises:

displaying a plurality of probabilities indicating a likelihood of the individual opening the care gap within a time span.

20. A non-transitory computer-readable medium having processor-executable instructions stored thereon, wherein the processor-executable instructions, when executed, facilitate:

obtaining population information for a plurality of individuals associated with an enterprise organization;

filtering the population information using a plurality of care gap cohorts to determine a subset of the population information for each of the plurality of care gap cohorts;

training a plurality of care gap machine learning-artificial intelligence (ML-AI) models based on the subset of the population information such that each of the plurality of care gap ML-AI models is associated with one or more care gap cohorts from the plurality of care gap cohorts;

determining to retrain a first care gap ML-AI model, of the plurality of care gap ML-AI models, based on a first care gap cohort, of the plurality of care gap cohorts, having insufficient data to train the first care gap ML-AI model;

based on the determination, combining a first subset of the population information associated with the first care gap cohort with a second subset of the population information associated with a second care gap cohort from the plurality of care gap cohorts to obtain combined population information;

retraining the first care gap ML-AI model based on the combined population information;

obtaining individual information of an individual, wherein the individual information indicates one or more medical conditions of the individual and a care gap of the individual indicating a gap in time that the individual has a lapse in receiving medical care for the one or more medical conditions;

selecting the first care gap ML-AI model, from the plurality of care gap ML-AI models, based on comparing the gap in time that the individual has the lapse in receiving medical care for the one or more medical conditions with the plurality of care gap cohorts;

determining care gap information of the individual based on using the first care gap ML-AI model and the individual information; and performing one or more care gap interventions based on the care gap information.

\* \* \* \* \*